(12) United States Patent  
Underwood

(10) Patent No.: US 6,550,356 B1  
(45) Date of Patent: Apr. 22, 2003

(54) TATTOO TECHNOLOGY

(76) Inventor: Keith A. Underwood, 621 E. 138th St., Burnsville, MN (US) 55337

( * ) Notice: Subject to any disclaimer, the term of this patent is extended or adjusted under 35 U.S.C. 154(b) by 288 days.

(21) Appl. No.: 09/662,738

(22) Filed: Sep. 15, 2000

Related U.S. Application Data

(60) Provisional application No. 60/154,704, filed on Sep. 18, 1999.

(51) Int. Cl.$^7$ ............................. B41B 1/00; A61B 17/20
(52) U.S. Cl. ............................. 81/9.22; 81/438; 30/362; 128/253
(58) Field of Search .................... 81/9.22, 438; 30/362, 30/366; 606/186, 169; 128/253

(56) References Cited

U.S. PATENT DOCUMENTS

| | | | |
|---|---|---|---|
| 1,724,812 A | | 8/1929 | Waters |
| 4,159,659 A | * | 7/1979 | Nightingale ............... 81/9.22 |
| 4,203,438 A | | 5/1980 | Shiu |
| 4,204,438 A | * | 5/1980 | Binaris et al. ............... 81/9.22 |
| 4,782,725 A | | 11/1988 | Spaulding |
| 4,914,988 A | | 4/1990 | Chang |
| 5,054,339 A | * | 10/1991 | Yacowitz ................. 81/9.22 |
| 5,165,488 A | | 11/1992 | Liu |
| 5,401,242 A | * | 3/1995 | Yacowitz ................. 604/48 |
| 5,551,319 A | | 9/1996 | Spaulding et al. |
| D380,046 S | * | 6/1997 | Domanowski ............. D24/144 |

* cited by examiner

*Primary Examiner*—Joseph J. Hail, III
*Assistant Examiner*—Anthony Ojini
(74) *Attorney, Agent, or Firm*—R. C. Baker & Associates, Ltd.

(57) ABSTRACT

The composite battery-integrated tattooing machine totally avoids a clip cord and the drag associated with it. The new machine comprises a base frame for removably holding a needle bar housing assembly, a tattoo needle assembly removably mounted to reciprocate within the needle bar housing, a reciprocating motion generator having at least one electromagnet and a make and break mechanism for effecting reciprocating motion of the tattoo needle assembly, a battery, a rheostat, and a switch for actuation of the reciprocating motion of the tattoo needle assembly. An important switch arrangement is radio operated; other switches are hand operated. Special subassemblies are provided for conversion of known professional tattooing machines into the new type having battery power integrated with the tattooing machine. Experts can now tattoo without the annoying drag of a clip cord.

19 Claims, 5 Drawing Sheets

TATTOO TECHNOLOGY

CROSS-REFERENCE TO RELATED APPLICATIONS

This application claims the priority benefit of provisional application Ser. No. 60/154,704 filed Sep. 18, 1999.

BACKGROUND OF THE INVENTION

This invention relates to improvements in tattoo technology, and particularly to compact battery-integrated tattooing machines, new subassemblies for providing battery integration to known tattooing machines, and to new methods for practicing the art of tattooing.

Professional tattoo artists demand high quality equipment. This has led such artists to an almost universal adoption of the type of tattooing machine (with but modest modifications) as described in Waters U.S. Pat. No. 1,724,812 of Aug. 13, 1929—a teaching more than 70 years old. A significant feature of the old Waters teaching is that it employs a vibrating armature bar for effecting reciprocating motion of the tattoo needle assembly, including the needle bar of that assembly. The important feature is that the needle assembly of the tattooing machine vibrates or reciprocates in a straight up and down line parallel with the longitudinal direction of the needle assembly, and this is to be distinguished from tattooing instruments that employ a rotating motor for effecting the needle reciprocation. The instruments that employ rotating motors tend to create a wobbly effect for the reciprocation of the tattoo needle. Such wobbling of the needle tends to cause an oval-type puncturing of the skin of a person undergoing the tattooing procedure and causes more tearing of the skin than necessary and much more than when the ideal tattooing instrument is employed that does not have wobbling of the needle. The ideal tattooing instrument—known for over 70 years—relies upon electromagnets and a make and break contact mechanism to effect reciprocation of the armature bar to which the needle assembly is directly connected and thus reciprocates as a unit with the armature bar.

What is amazing is that the use of a battery as an integrated part of a hand-held rotating motor tattooing instrument has apparently never triggered any consideration of a battery as an integrated part of hand-held professional tattooing equipment. Whatever the explanation, professional tattooing machines of the type capable of effecting un-wobbly reciprocation (where the reciprocation is effected by an armature bar vibrating over electromagnetic coils) have employed power units separate and remote from the tattooing instrument or machine and with the remote power connected by a clip cord to the tattooing machine. Also, a rheostat for adjusting the power supply and a foot switch for power have been part of the remote power unit for easy foot on and off operation to actuate the reciprocating needle motion while the tattoo artist is employing his or her hand carefully to move the needle tattooing instrument and create a tattoo. The problem, however, with these known professional equipment arrangements is that they are bulky and there is always a drag on the tattooing instrument or machine caused by the clip cord connection to the remote power unit. The drag tends to pull the tattooing instrument out of balance and interferes with the ability of the tattoo artist to create artistic tattoos of finite definition and proper depth for color retention, etc.

Despite the fact that the cord of the clip cord has been a complaint of tattoo artists for ages, no one has heretofore proposed any effective solution to avoid the clip cord and the drag caused by it. Suppliers of the type of tattoo equipment illustrated in the aforenoted Waters patent as well as the artists who use that type of equipment have seemingly concluded that the known bulky equipment (with clip cord and gauges and the like associated with it) is vitally necessary for the professional tattoo artist to get the strength of "hit" on the skin for proper ink penetration and that therefore a clip cord is required and thus no possible convenient equipment free of clip cord drag could ever be satisfactorily used to create truly artistic tattoos.

This invention changes that 70-year history and gets rid of the clip cord drag and clumsiness.

It has been found that regardless of the type of power unit employed, the power needed for operating professional tattoo machines of the type aforenoted must be at least about 9 volts and generally at least about 12 volts. When the voltage is lower, the needle reciprocation is weak and the definition desired by the tattoo artist is reduced and becomes unsatisfactory.

But the truly important point of this invention is the striking advantage provided by getting rid of the annoying clip cord drag for the true tattoo artist.

SUMMARY

This invention provides a compact tattoo instrument free of any drag by an electrical clip cord or the like, and an instrument adequately powered for high definition tattooing. A significant aspect of the solution to the old clip cord problem is not just integrating a battery into a compact unit. Much more is needed, for the control (and easy switch operation) has to be integrated into or associated with the compact unit in a manner not interfering with easy removal of the metallic barrel or needle bar housing as well as the tattoo needle assembly from the instrument for the purpose of effective, thorough sterilization. Thus, any finger switch integrated with the compact assembly has to be separate or separable from the barrel or needle bar housing and yet has to be accessible to the fingers of the operator or tattoo artist who also must grip the barrel or handle part of the needle housing in creating an accurate and fine definition tattoo.

An exceedingly important aspect of the invention is its teachings for electively positioning a switch useful for a tattoo operator in a manner suiting the operator's convenience and yet in a manner that maintains maximum accessibility for the operator creating a tattoo. The invention also gives the advantage of rheostat adjustment separate from a switch for controlling the reciprocation of the tattooing machine. The convenience of a finger switch and a flexible cable having the resilience to return to a preset condition is also a teaching of the invention.

And the convenience of remote radio control for a tattooing machine having a battery integrated in the structure of the machine itself is also a unique feature of the invention.

Still further, among the teachings and practices of the invention are special assemblies designed especially for attachment but removable attachment to tattooing machines of the professional type. And this is accomplished in a manner to enhance the economy of the professional tattoo artists in their conversion of existing equipment to the unique clip cord-free tattooing instrument or machine of the invention.

Still other advantages and benefits of this invention will be evident as this description proceeds.

DRAWING

FIG. 1 is a schematic diagrammatic side view of the new compact tattoo apparatus, with many details omitted from view so as to permit great clarity for the showing (the side view is frequently referred to herein as the "front" side);

FIGS. 2, 3, and 4 are schematic diagrammatic front, back, and rear views of a known waters-type tattooing machine with special detail clearly illustrated so as to enhance understanding of the teachings of this invention dealing with the varied attachable subassemblies for integrating battery power with a tattooing machine in a manner that provides a total composite easily handled by the tattooing artist without having parts slipping around or shifting and causing disruption of balance; it is to be noted that the needle bar housing as well as the tattoo needle assembly have been omitted from FIG. 2 et seq. solely to reduce the space needed for illustrations; those known elements are show n and illustrated in FIG. 1;

FIG. 8 is especially important as an illustration of a radio-controlled switch operation for the tattoo machine;

Figures 5A, 5B, 6:
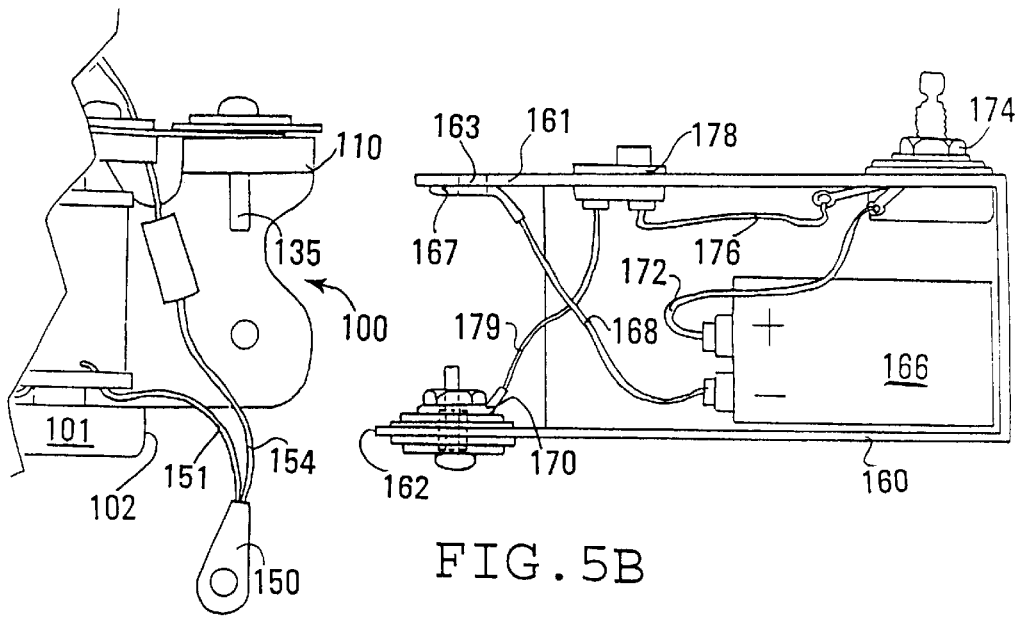
FIG. 5A is a front view of the rear part of a known tattooing machine.
FIG. 5B is a front view of one type of subassembly for attachment to the known tattooing machine; and these figures are shown in a spaced relationship to enhance understanding of the way the subassembly is attached to the known tattooing machine.
FIG. 6 illustrates a composite battery-integrated tattooing machine of the invention formed by attaching the subassembly of FIG. 5B to a known tattooing machine as illustrated in FIG. 5A.
Figure 10:
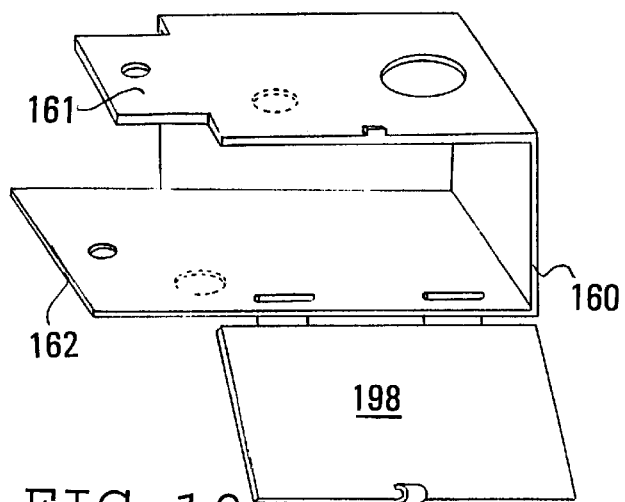
Figure 7:
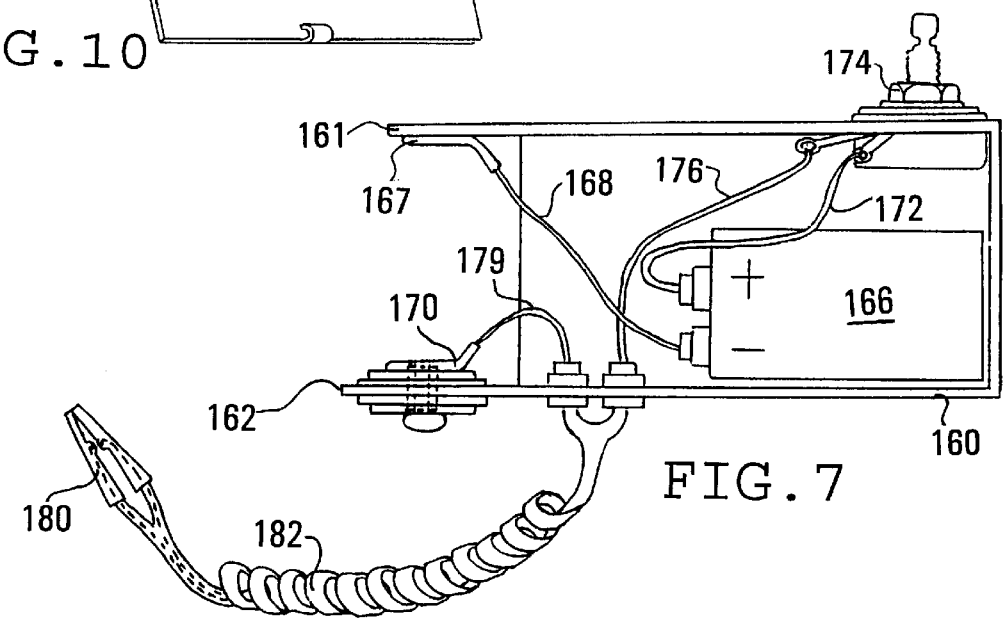
FIG. 7 is an alternate form for a subassembly attachable to a known tattooing machine in the same manner as illustrated in FIG. 6.
Figure 8:
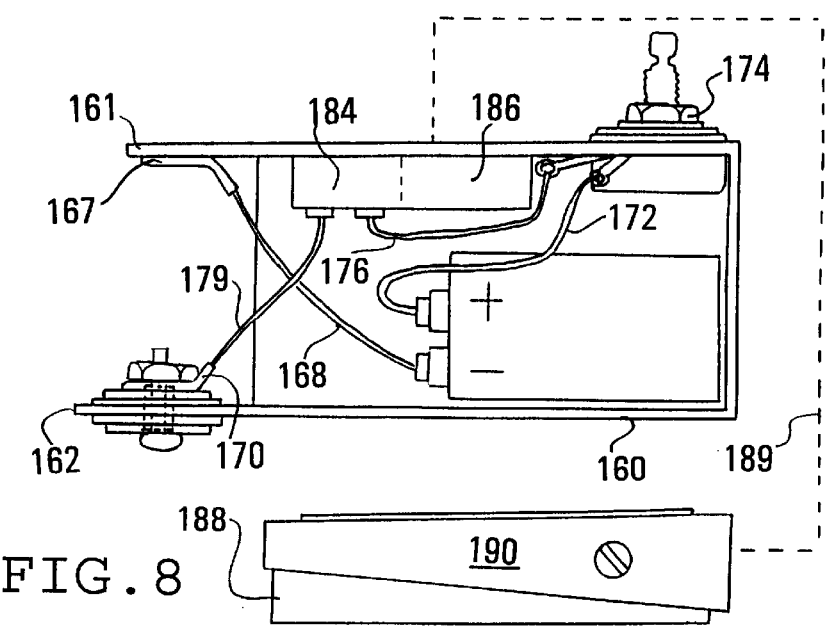
FIG. 8 is a still further altered subassembly attachable to a known tattooing machine in the same manner as illustrated in FIG. 6.
Figure 9:
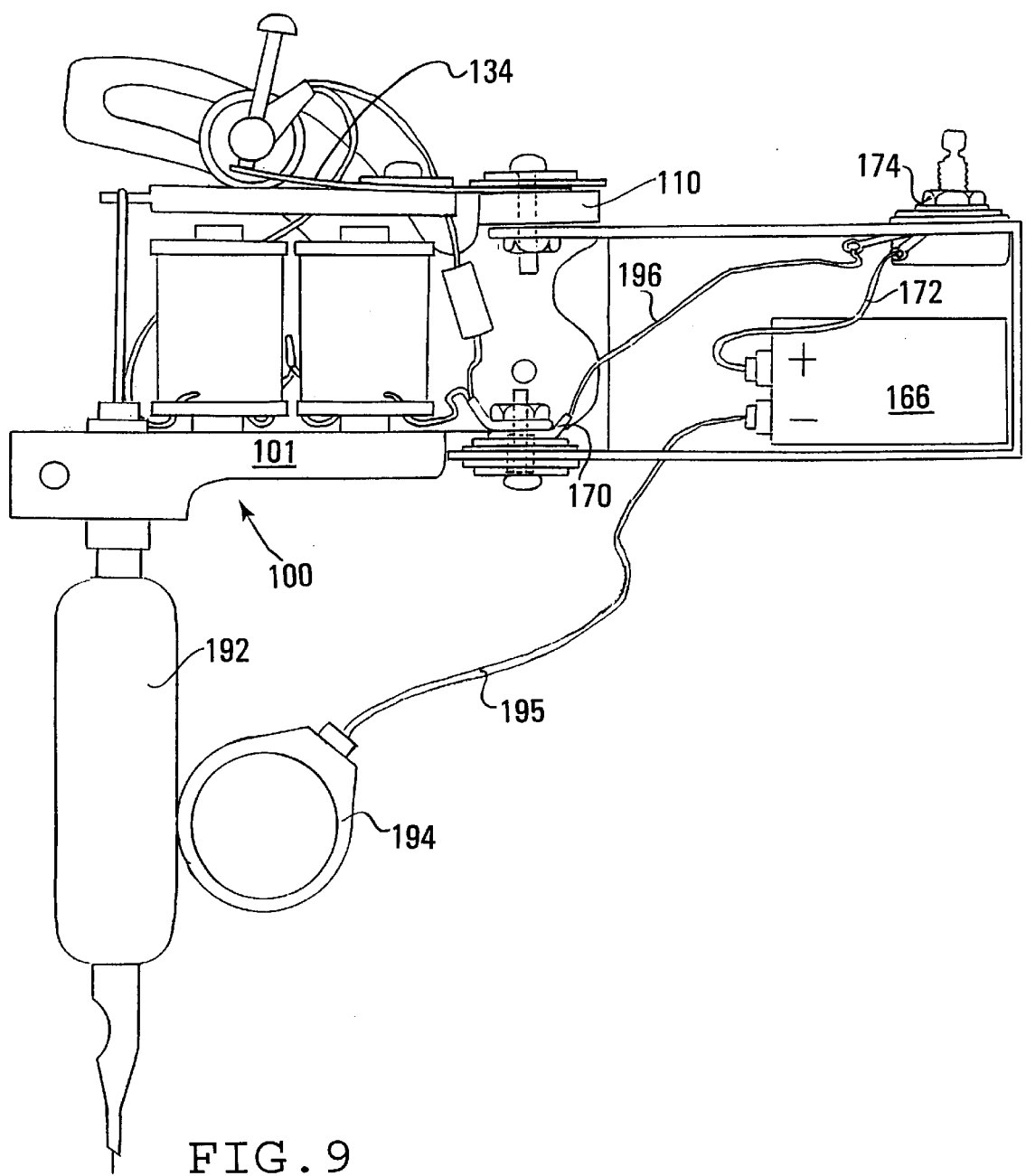

FIG. 9 is a still further possible arrangement for a subassembly attachable to a known tattooing machine in the manner illustrated in FIG. 6, and illustrates a front view of a battery-integrated tattooing machine having a grounding ring for contact with a grounded needle bar housing to form a switch for operation of the composite tattooing machine; and FIG. 10 is a schematic perspective view of a box-like subassembly housing that functions as a subframe suitable for the subassemblies illustrated in FIGS. 5 through 9.

DESCRIPTION OF PREFERRED EMBODIMENT(S)

The teaching of this invention incorporates basic features from the classic time-tested tattooing machine as described in Waters U.S. Pat. No. 1,724,812 of August 132, 1929; and for that reason, the teaching of that Waters patent is here incorporated by reference, with the caveat that the Waters teaching of a switch integrally united to the needle bar housing is unsatisfactory for reasons of sanitation—it precludes proper and effective sterilization.

Figure 1:
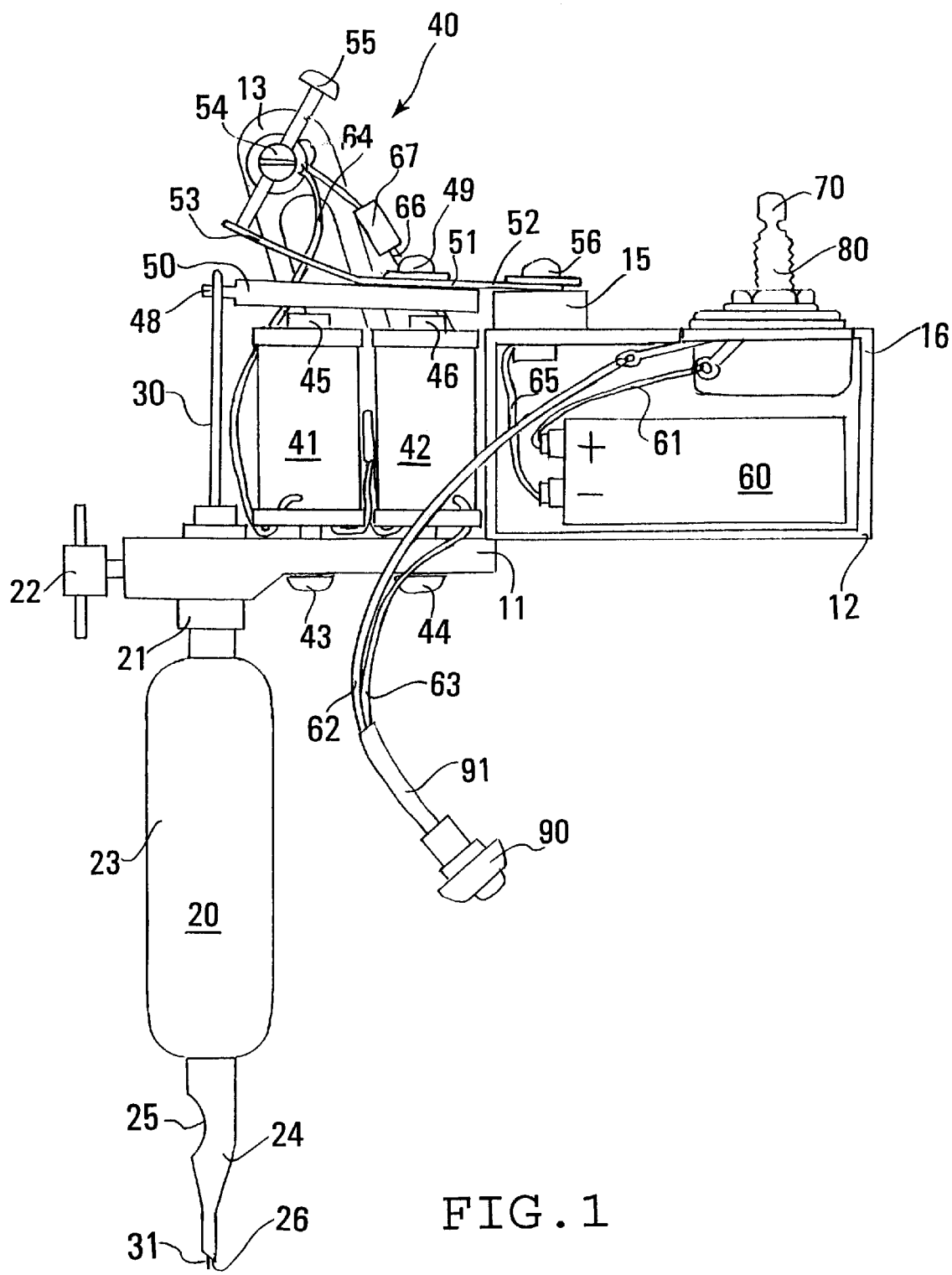

Referring to FIG. 1, the new compact tattoo device of this invention comprises a frame 10, a barrel or needle bar housing 20, a needle assembly including a needle bar 30, a generator of reciprocating motion 40, a battery 60, a rheostat 80, and a switch 90. The switch is illustrated as a finger switch 90 in FIG. 1. A master switch 70 on the rheostat 80 is not preferred for the reason that tattooing artists like to use the rheostat to set the rate of reciprocation for the needle and then keep it that way as they turn the machine on and off in conducting a tattooing procedure.

The frame 10 may take various forms but, as illustrated, it has a horizontal base bar or flange 11 with a horizontal rearward extension 12 serving as a base for mounting a battery 60. At the back of the elements (as viewed in FIG. 1) are two upright standards (neither of which is shown with great clarity, but both of which project upward from the back side of the horizontal base 11). One standard 13 supports at its upper end a horizontal binding post 54 or foundation for an adjustable contact screw 55, and the other upright standard terminates at its upper end in a horizontal flange 15 (also called a back shelf) serving as a mounting or grounding foundation for the flat portion 52 of a leaf spring 51 having an angular tapered portion 53 that contacts the contact screw 55. A fastener 56 such as a bolt or screw extends through the flange part or back shelf 15 of the rearward upright standard for the frame and braces a box-like rear portion 16 of the frame against shifting movement.

The barrel or needle bar housing 20 has an annular or cylindrical upper portion 21 which extends through a generally cylindrical hole (not shown) in the horizontal base bar 11 of the frame; and a suitable screw 22 or fastening member is operable through the end of that base bar 11 for securing that annular portion or small cylindrical portion 21 of the housing 20 in position on the base bar 11. This needle bar housing 20 has a rather enlarged handle 23 (e.g., barrel) portion, generally provided with serrations or other roughness on the surface so as to permit easy non-slip gripping by the tattoo artist. Below that barrel-like portion 23 for hand gripping is the ink well portion 24 of the needle housing (generally filled by dipping the end into ink of desired color), and of course a small area can be noted as an opening 25 for washing ink out of the well portion 24 (as by using a solution such as alcohol or water). To be noted is that the lower tip 26 of the needle bar housing forms the exit opening for ink from the ink well. It suitably may be angular and preferably is at an angle to the length of the housing 20. An angle gives convenience for the positioning of the tip on a surface of skin to be marked with a tattoo. But it is also possible that the angularity may be substantially less than that illustrated, or even rather perpendicular to the length of the housing.

The tattoo needle bar 30 extends through the needle bar housing and the needle assembly 31 (of one or more needles) at its end projects outwardly at the lower tip end of the housing just sufficiently for penetration into the depth of the skin of a human or other creature to be marked with a tattoo (at the proper depth for retention of the ink without total penetration through all skin layers and resulting unwanted dissipation of the ink). Tattoo needles of a variety of configurations are useful. Some have a single needle point; others may have several needles and a variety of needle points or configurations. The needle bar 30 is equipped with an eye (not shown) at its upper end, and that eye is slipped over a projecting stud 48 at the end of the armature bar 50. The armature bar 50 is capable of reciprocating vibrations so as to move the needle up and down with minimal, if any, sideways movement. The wobbling sideways movement of rotating motor reciprocators is totally avoided, and the unnecessary tearing of skin and extra bleeding caused by wobbling reciprocating needles is avoided by the illustrated apparatus.

The apparatus 40 for creating reciprocal motion ideally relies upon electromagnets 41 and 42 for creating a vibrating effect and therefore reciprocal motion for the needle bar 30. (Other arrangements have been suggested over the years, but they create additional problems and have been considered unsatisfactory for the professional tattoo artist.) The electromagnetic approach for creating a vibratory reciprocal motion for the needle bar seems to be the most reliable without introducing additional problems for satisfactory reciprocal motion. Electromagnets 41 and 42 are mounted on the base frame portion 11 of the device as by fasteners 43 and 44 in a suitably spaced relationship where more than one is employed. A make and break mechanism is used for the vibratory reciprocation of the needle assembly. The make and break mechanism has an armature bar 48 above the electromagnets, and the armature bar is secured to the underside of the flat portion 50 of the leaf spring 51 so that the armature bar 48 actually is in slightly spaced relationship to the armature cores 45 and 46 of the electromagnets. The tapered angular portion 53 of the leaf spring 51 abuts against the electrical contact adjustment screw 55 in the post 54, and the electrical circuit for the electromagnets extends through the adjustable contact screw 55 to the leaf spring 51 so that the electromagnets are charged when the leaf spring abuts the screw 55. Charged electromagnets pull down the leaf spring including its front tapered portion by virtue of the fact that the armature bar (to which the leaf spring is attached by mounting fastener 49) is drawn into contact with the central armatures 45 and 46 of the electromagnets. But when that happens, the current through the electrical contact member or screw 55 to the front tapered portion 53 of the leaf spring 51 is broken by the space between those elements, and thus the electromagnets lose their power and the armature bar at the end of the leaf spring is pulled back up by virtue of the biasing action of the leaf spring per se.

To be noted is that the armature bar is solely mounted to the leaf spring 51 and the leaf spring has its sole mounting at the back outer end of its flat portion 51. That flat end is fixed by fastener 56 (e.g., bolt) to the horizontal flange 15 of the frame. Flange 15 is the back shelf of the frame, and that shelf is a feature of all presently popular professional tattooing machines. The shelf is usually made of electrically conductive iron and thus serves electrically as a ground terminal or location.

An on/off switch 70 located on a rheostat 80 is not desired. An important aspect for the invention is the power regulator or rheostat that can be adjusted at the beginning of a tattooing procedure and not disrupted by turning the tattooing machine on and off.

The finger switch 90 is an important element in the embodiment of the invention as illustrated in FIG. 1. The switch should not be in a fixed immovable position on the barrel or needle bar housing. It should be adjustably positionable. As before noted, the barrel or needle bar housing in its entirety must be removable from the device for sterilization purposes, just as the needle itself must be removable for sterilization purposes. On the other hand, the ideal finger switch has to be operable by a finger of the operator on the same hand as the operator employs for gripping the barrel enlarged handle portion 23 of the ideal housing in conducting a tattoo operation. Thus, the cable 91 at the end of which the finger switch is located has to be flexible, although it may be of a springy, flexible character in the sense that the cable (i.e., cable sheath covering the wires to the finger switch) may have a preformed curvature or contour just sufficiently stiff so that the cable will always be biased in that particular preformed shape whenever the tension of moving the cable is removed. An option, of course, is to provide a little hook on the barrel handle portion of the needle bar housing for temporarily lodging the finger switch or the cable of the finger switch in a position on the handle barrel portion for convenient access when the operator grips the housing for tattooing operations.

Frequently, the making of a tattoo causes the tattoo apparatus to become smeared or contaminated with ink and even blood. It is thus important to cover the finger switch and cable, and even other associated parts of the tattoo machine, with a protective film or plastic bag so as to prevent cross-contamination and to contribute to sanitation.

The wiring diagram is only crudely illustrated in FIG. 1, but it should be noted that power from the battery 60 first goes to the rheostat 80 via a line such as that marked 61, then from the rheostat to the finger switch 90 through a line 62. From the finger switch, the power passes through a line 63 to the coils or electromagnets, and then from the electromagnets the power moves through a line 64 to the front binding post, where it passes through the adjustment contact screw 55 to the angular portion of the leaf spring 51 and then back to the back shelf 15 of the frame (which is grounded). From there it passes back to the battery through line 65. Another line 66 extends between the binding post 54 and line 63. The connection of line 66 to line 63 is not shown in FIG. 1. A capacitor 67 is interposed in line 66 to facilitate holding a charge to enhance the effectiveness of the vibratory reciprocating action and minimize sparking.

A significant feature of the invention is the reduction of parts that are necessary for a truly effective and professional tattoo machine. Most important is the fact that a clip cord is no longer necessary, and the drag of it on the tattoo instrument as the tattoo artist is creating a tattoo is totally avoided.

The new battery-integrated tattoo apparatus of the invention permits a tattoo artist to perform the tattoo operation or procedure with supreme convenience at remote locations. The new device is truly a portable, completely self-contained and battery-integrated tattoo machine.

Any suitable battery and battery connections may be employed, with preference for 9 volt batteries and upwards of up to 12 and even 15 volt batteries or more, and preference for direct current (not alternating current), all of which can provide the tattoo artist with the greatest of convenience in satisfying customer predilections and proper tattoo definition. Rechargeable batteries are preferred.

Ideally, the needle bar and the needle bar housing assembly are made of stainless steel or any similar high-quality metal capable of thermal or autoclave sterilization.

To reiterate, the new tattooing device of FIG. 1 comprises a base frame for removably holding a needle bar housing assembly so as to permit easy removal of it for sterilization purposes, a tattoo needle assembly (of any style as desired) removably mountable to reciprocate within the needle bar housing, a reciprocating motion generator having at least one electromagnet and a make and break mechanism for effecting reciprocating motion of the tattoo needle assembly, a battery, a rheostat, and a flexible cable-mounted finger switch for finger actuation of the reciprocating motion of the tattoo needle assembly.

A summary description of a currently popular known tattoo machine of the prior art will now be given by reference to FIGS. 2, 3, and 4.

The frame 100 has a horizontal base bar or flange 101 terminating at its rearward end 102 as a flat edge perpendicular to the length of the base bar. At its forward end 103, the base bar is equipped with a bifurcation (not shown) of the frame and a fastener 104 for tightening the bifurcated ends together. A channel 105 through the forward portion of the frame is for receipt of the upper portion (suitably annular or cylindrical in shape) of the needle bar housing as described in connection with FIG. 1, and the screw or fastener 104 is for gripping the bifurcated ends of the frame together so as to rigidly hold the needle bar housing for needle reciprocation as described in connection with FIG. 1.

An upright standard 106 somewhat in the nature of a contoured back wall (see FIG. 3) extends up from the base bar 101. This wall 106 is a continuation of the base bar 101 of the frame and has been equipped with a lower rearward hole 107 which becomes unnecessary for the improvements of this invention, but has in the past been employed as the mounting point for a post for receipt of one of the terminals of a clip cord heretofore required. The upright standard at the back of the machine has a curved forward projection 108 that lies in the same plane as the mass of the upright standard. The curved forward projection has a curved slot 109 in it. Also contoured at the upper rearward portion of the upright standard is another structure, namely the structure known as the back shelf 110. The back shelf 110 is horizontal and thus is perpendicular to the vertical upright standard and extends toward the front of the machine, as illustrated in FIG. 1. Put another way, the plane of the back shelf 110 is parallel with the plane of the horizontal base bar.

Iron frames of cast iron or steel appear to be very popular and are electrically conductive and thus serve well for grounding an electrical circuit, but it is entirely possible to employ other materials for the fabrication of a suitable frame, including materials that are not electrically conductive. Thus, depending on the material of the frame, different arrangements for electrical insulation for maintaining appropriate conductivity and lack of conductivity may be necessary, as is well understood by those skilled in the art. As an example, while the back shelf can serve well as a grounding terminal for the electrical circuitry, and thus is preferably electrically conductive, it is quite possible to employ an insulating back shelf as the foundation support mounting for an electrically conductive leaf spring, and then employ an electrically conductive fastener or bolt to maintain integrity for the grounding return of a complete electrical circuit such as described hereinafter.

The frame 100 supports a generator of reciprocating motion. This generator has at least one electromagnet 120, and two 120 and 121 are shown mounted in electrically insulated manner on the frame, specifically on the horizontal base bar 101 of the frame. The electromagnets are properly called electromagnetic coils, and are fixed at a core portion thereof so as to project perpendicularly upward from the base bar of the frame. Any suitable mounting may be employed. The upper end of the coils includes an electromagnetic core 122 and 123 that is subject to magnetic activation and deactivation (i.e., to a magnetic charge and lack of charge) in an extremely rapid manner—all depending on the passage of electrical current through the electromagnets.

Above the electromagnetic coils is a make and break mechanism 130 having several special features. First, an important feature is that of the electrical contact member 131 mounted in spaced relationship above electromagnetic coils. The contact member ideally is an adjustment screw extending through a horizontal post 132. Post 132 is mounted for slide adjustment along the hollow curved hole 109 or arc in the forwardly projecting portion 108 of the upright standard.

A leaf spring assembly 134 (whether consisting of one or two or more leaf springs connected in a series relationship) is mounted at one end to the back shelf 110 of the frame (as by a fastener or bolt 135), and has a free end that extends between the electromagnetic coil or coils and the contact member or adjustment screw 131. The free end of the leaf spring is biased toward electrical contact with the contact member or adjustment screw 131.

Under the leaf spring 134 and insulatively mounted to it as by a fastener screw or bolt 136 (or by more than one fastener along the length of the leaf spring) is an armature bar 138. This armature bar is secured in a fixed manner under the leaf spring assembly and is actuated by the electromagnetic coils so as to cause make and break electrical contact of the leaf spring with the electrical contact member or adjustment screw 131. This make and break electrical contact of the leaf spring assembly with the contact member is exceedingly rapid. It generates the needed reciprocating motion of uniform up and down character. The electromagnets are charged when the leaf spring abuts the adjustment screw, but charged electromagnets pull down the leaf spring because the armature bar is drawn into contact with the central armatures or cores of the electromagnetic coils. When that happens, the current through the adjustment screw and leaf spring is broken, the electromagnetic coils then lose their charge, and the armature bar goes back up into contact with the contact member 131 as a result of the biasing action of the leaf spring.

A stud 140 at the very end of the armature bar 138 is used for mounting the needle bar of a tattoo needle assembly to the armature bar. An eye opening at the upper end of the needle bar is slipped over the stud and the result is that the needle assembly in the needle bar housing held by the frame is in essence held in a perfect alignment for reciprocation without wobbling.

Figure 2:
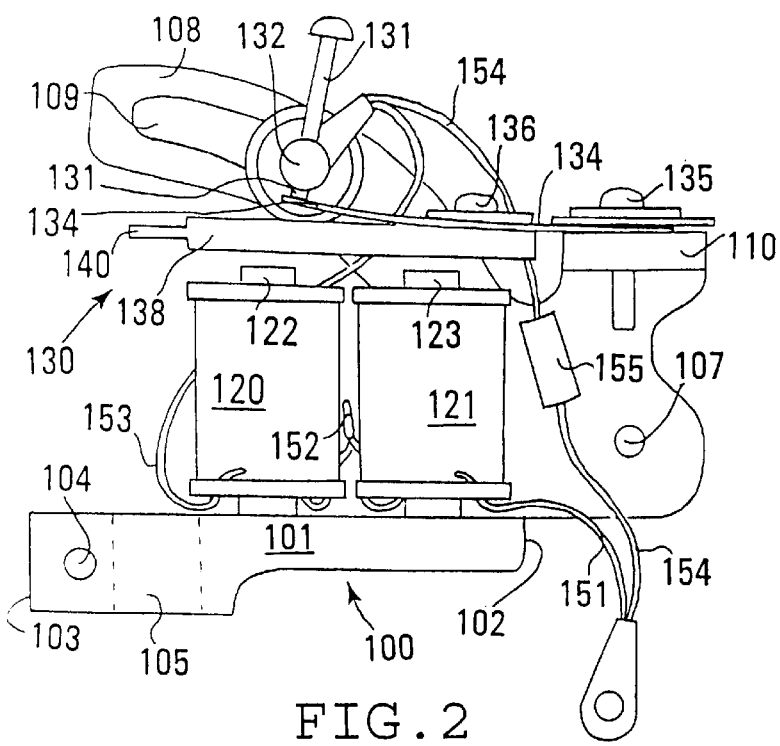
Figure 4:
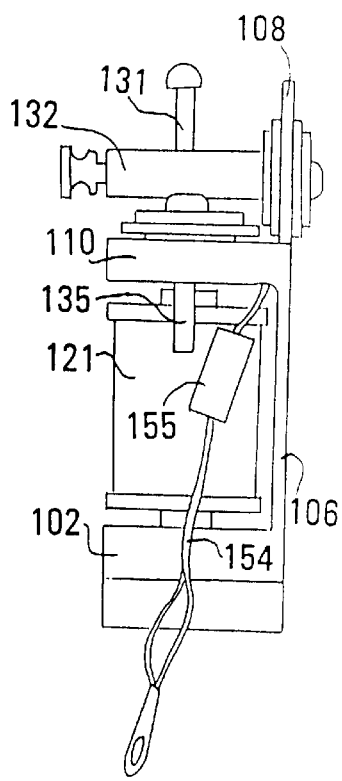
Figure 3:
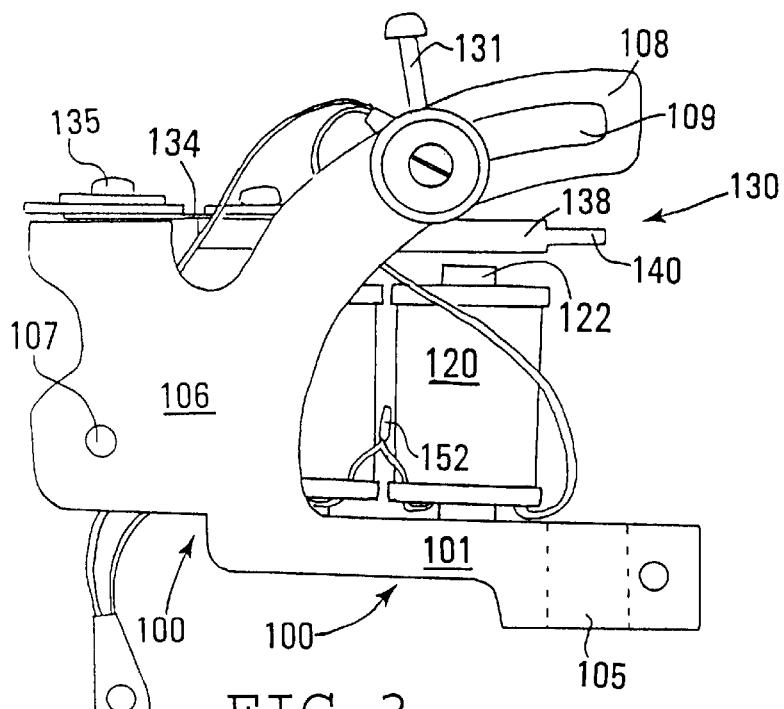

The circuitry illustrated in FIGS. 2, 3, and 4 is that of a ground at back shelf 110 and an electrically positive terminal or connector 150. The positive terminal 150 is referred to as an energy-receiving terminal in this specification since it is the connecting portion on the known tattooing machines for the positive pole of current. (A clip cord connection has heretofore been applied between the energy-receiving terminal or connection 150 and the grounded back shelf 110.) Current from the positive connector 150 passes via line 151 to the coil of one electromagnet 121 and then through a connector line 152 to the adjacent electromagnet 120. From the adjacent electromagnet 120 a line 153 extends to the electrical contact screw member 131 for the leaf spring. It then flows through the leaf spring 134 to the ground suitably illustrated by a conductive bolt 135 fastening the leaf spring 134 to the back shelf 110. A line 154 from the connector or positive terminal to the electrical contact adjustment screw member 131 is modified by an interposed capacitor 155 that can hold and release a charge and thus increase the effectiveness of the reciprocating motion generator. The capacitor also reduces the tendency towards sparking at the make and break mechanism.

Referring now to FIGS. 5A and 5B, only a fragment of a known tattoo machine is illustrated in FIG. 5A, and that portion illustrated is the portion to which the subassembly of 5B is capable of removable fixed attachment. The schematic illustration of FIG. 5B includes a subframe of 160 box-like character (and that subframe of box-like character may be as illustrated in FIG. 10).

The subframe 160 has a forward shelf 161. Shelf 161 is in the nature of a horizontal projecting shelf. It is readily mate-able with the back shelf 110 of known tattoo machines. Specifically, the forward shelf 161 is adapted to underlay against the underside of the back shelf of the base frame 100 of known tattooing machines. In effect the forward shelf 161 of the subassembly and the back shelf 110 of the known tattooing machine are capable of being removably fastened together in a manner such that the shelves are in overlapping relationship and in a manner such that the subframe 160, which is integral with the forward shelf 161, becomes part of the total composite tattooing machine. Thus, the subframe, when united to the known tattooing machine frame, will move with the tattooing machine frame as a structure totally unified and integrated with it. It is important to have the subframe of the subassembly unified with the tattooing machine in a manner preventing wiggling and shifting of the subframe simply because any such wiggling or shifting could serve to disrupt the balance the tattoo artist has a right to expect for a composite integrated tattooing machine. A feature of the subframe enhancing stabilized mounting of it to the base frame 100 of the tattooing machine is incorporated at a lower portion as a projecting abutment edge 162. The abutment edge 162 has a flat surface extending along a plane perpendicular to the lengthwise direction for the subframe (i.e., the extension direction rear of the subframe). The abutment edge 162 is adapted to press against the rearward end 102 of the base bar 101 of the base tattoo machine frame 100. That rearward edge 102 lies in a plane perpendicular to the length direction of the base bar of the base frame of the tattoo machine.

Within the subframe is mounted a battery 166 having negative and positive terminals. The battery should be one of at least 9 volts, and preferably at least 12 volts or more. Recharged batteries are preferred.

A subframe ground terminal 167 is electrically connected through line 168 to the negative terminal of the battery and that subframe ground terminal, as illustrated in FIG. 5B, has a bolt hold 163 (extending also through the front shelf 161) for receiving the shaft of a fastening bolt for a fastening connection to the back shelf of the tattoo machine frame.

An energy terminal 170 is mounted insulatively on the subframe by any suitable fastener 171. The energy terminal 170 is for electrical connection to the energy-receiving terminal 150 of the tattooing machine, and a subframe energy line extends between the positive terminal of the battery and the energy terminal on the subframe. However, a rheostat is interposed in that energy line and a switch is also interposed in that energy line. Thus, the energy from the positive terminal of the battery flows first in the line 172 to the rheostat 174 and then in the line 176 to the switch 178 and from the switch through a line 179 to the energy terminal 170 that is ready for electrical connection to the energy-receiving terminal of the tattooing machine. The rheostat permits adjustment of the level of energy passing through the energy line so as to permit adjustment of the level of energy fed to the reciprocating motion generator in a manner as desired by a tattoo artist. The level of energy for the reciprocating motion generator depends upon the nature of the needle assembly selected for use in the tattooing machine, and experts in tattooing desire to set the rheostat and the amount of energy flowing to the reciprocating motion generator with great care, after which they prefer not to have the rheostat changed except as they may want change to it during a tattooing procedure. Thus, a switch on the rheostat or a rheostat with adjustment function also carrying a switch function is not desired. The preferable arrangement is a separate switch controlled by the operator by simply pressing a button or by shifting the position of the switch from on to off, etc. The switch in FIG. 5B is one mounted on the subframe.

In FIG. 6, the subassembly of 5B is united to the base frame 100 of the tattooing machine by fixing the forward shelf 161 of the subframe under the back shelf 110 of the tattooing machine frame in a rigid manner, as by the nut and bolt assembly 135 illustrated in FIG. 6. The abutment edge 162 on the subframe rests against the rear edge of the base bar frame 101 and helps to maintain the entire subassembly as a completely integrated non-wobbly structure with the tattooing machine, with no need for any annoying clip cord. Thus, the professional tattoo artist is able to conduct a tattoo procedure in a convenient manner without clip cord drag—an accomplishment long desired.

Referring now to FIG. 7, the features of the subassembly illustrated in FIG. 5B are substantially duplicated in FIG. 7, except for a significant change. Specifically, in FIG. 7, the switch 180 for on and off operation (to open and close the electrical circuit) is at the end of a flexible cable 182. It can be opened and closed by the fingers of the same hand that the artist uses to grip the needle bar housing during a tattooing procedure. Interestingly, the flexible cable 182 illustrated in FIG. 7 is one that is stiffened just sufficiently to have a contour (e.g., comparable to a coiling for a telephone line) to which the coiled cable returns after being flexed or pulled to a different shape or contour during use in a tattooing procedure.

A still further switch arrangement is illustrated in FIG. 8 where the subassembly is, apart from the switch arrangement, substantially identical to that illustrated in FIG. 5B. What is interesting in respect to FIG. 8 is that the switch 184 is radio operated, there being a radio receiver 186 mounted with the switch in the subframe of the subassembly, and a radio transmitter 188 in a foot switch 190 that may be placed at a remote location. A simple radio wave 189 can effect on and off operation of the control switch 184 for machine operation, and a variety of settings for radio apparatus can be used so that artists working in close proximity need not interfere with each other's tattooing machine operation. Any suitable power may be employed for operation of the radio transmitter in the foot switch. Thus, the body of the foot switch may incorporate a battery or may have a connecting line to some other source of power remote from the foot switch per se.

The radio-operated approach for switching as illustrated in FIG. 8 is exceedingly convenient for conducting tattooing procedures. A composite tattooing machine incorporating the subassembly of FIG. 8 is little changed in its total weight and balance simply because the subassembly is easily manufactured with lightweight components. The frame need not be formed of any conductive metal. It may be formed of lightweight plastic. The foot pedal switch is something that professional tattoo artists are accustomed to use as the controlling switch for a clip cord connected to their tattooing machines. Thus, a radio-transmitting foot switch requires little change of thinking for the artist—except the change to turn the tattooing machine on by one click of the foot switch and to turn it off by another click. Continuous pressing of the foot switch to maintain power to a tattooing machine is unnecessary with radio control of the switching operation from a remote location.

FIG. 9 presents a still further subassembly illustrating an alternative for switching while still retaining many features as illustrated in FIG. 5A. In FIG. 9, the needle bar housing 192 of the tattooing machine functions as a ground terminal in the electrical circuit, and a grounding conductive ring 194 that the tattoo artist may place on his or her finger is connected through a line 195 to the grounding negative terminal of a battery. The result is that when the tattoo artist puts the ring against the needle bar housing, the ground connection for the circuit is completed and thus the ring and needle bar housing serve as the switch elements for the embodiment illustrated at FIG. 9. The "off" position for the switch is achieved by simply separating the ring from the needle bar housing. For this switch to work properly, it is preferred that the entire base frame 100 of the tattooing machine be formed of conducting material (such as a metal of the ferrous type) so that the grounding from the back shelf 110 mounting for the leaf spring 134 can be carried to the handle part of the needle bar housing 192 for the ring contact as illustrated. The significant point is that the switch is at the grounding side of the circuit for tattooing machine operation. Thus, the positive or energy side includes a direct connection line 196 from the rheostat 174 to the energy terminal 170 of the subframe. The ring should be detachable for effective autoclave sterilization.

The subframe for a subassembly may take the form of a box or the like as illustrated in FIG. 10. The box-like subframe of FIG. 10 includes the forward front shelf as well as the abutment edge of the subassembly. A hinged door 198 may be used to close the box-like subframe so as to place all components of the subframe within an enclosure somewhat protected against contamination from spattering of blood or splashing of any ingredient or materials present during a tattooing procedure. Holes or weak "knock-out" panels (illustrated by discontinuous lines) may be used as mounting places for components as discussed for the subassemblies.

Subassemblies as described permit the tattoo artist to retain equipment already purchased and incur only the expense of converting existing equipment into a composite tattooing machine with power integrated as part of the tattooing machine itself. That approach can satisfy the tattoo artist's desire for economy. But it is also to be emphasized that completely newly manufactured tattooing machines incorporating the subassembly as an integrated part of the tattooing machine, without removability or disconnectability for the subframe, are also contemplated by the invention. Thus, when the subassembly is incorporated as part of the total tattooing machine on initial manufacture, it can be convenient for the manufacturer to fabricate the total base frame for the tattooing machine as well as the subframe as part of one complete integrated frame, and to simplify electrical connections illustrated in FIG. 5A at the ground and energy terminals.

New integrated power tattooing machines of the invention permit an improved method for a tattooing procedure wherein, after gripping the needle bar housing for tattooing, the artist conducts the tattooing procedure without any drag of a clip cord connected to the tattooing machine from a remote power source or any other source and thus without any drag interfering with the operator's hand movement during the tattooing procedure. Further, a tattooing artist for the first time can turn the tattooing machine on or off from a remote location, and can adjust the level of energy passing through the electrical circuit of the tattooing machine by simply turning a rheostat mounted on the machine itself. Such features give the artist extraordinary advantages long desired.

Those skilled in the art will readily recognize that this invention may be embodied in still other specific forms than illustrated without departing from the spirit or essential characteristics of it. The illustrated embodiments are therefore to be considered in all respects illustrative and not restrictive.

That which is claimed is:

1. A compact battery powered tattooing machine comprising
    (i) a frame having forward and rearward locations plus a horizontal base bar and a back shelf,
    (ii) a needle bar housing removably mounted on said frame at a forward location,
    (iii) a tattoo needle assembly including a needle bar supported by said needle bar housing in a manner for reciprocating motion of said entire tattoo needle assembly,
    (iv) a generator of reciprocating motion mounted on said frame for effecting reciprocating motion of said tattoo needle assembly, said generator including
        (a) at least one electromagnet mounted on said base bar and
        (b) a make and break mechanism, said make and break mechanism including
            (b-1) an electrical contact member mounted in spaced relationship above said electromagnet, plus
            (b-2) a leaf spring assembly mounted at one end to said back shelf of said frame and having a free end extending between said electromagnet and said contact member, with said free end biased toward electrical contact with said contact member,
            (b-3) plus an armature bar secured to said leaf spring assembly and actuated by said electromagnet to make and break electrical contact of said leaf spring assembly with said contact member in an exceedingly rapid manner to thereby generate said reciprocating motion,
    (v) said tattoo needle assembly being connected to said armature bar for direct receipt of said reciprocating motion,
    (vi) a battery of at least 9 volts carried by said frame at a rearward location and having a positive terminal and a negative terminal,
    (vii) an electrical circuit carried by said frame for operating said reciprocating motion generator, said electrical circuit including an energy line connected to the positive terminal of said battery and a ground terminal connected to the negative terminal of said battery,
    (viii) a rheostat interposed in said electrical circuit on said frame for adjusting the level of energy passing therethrough so as to alter the level of the action by said reciprocating motion generator in a manner dependent upon the nature of the tattoo needle assembly selected for use in the tattooing machine, and
    (ix) a switch carried by said frame and interposed in said electrical circuit to open and close said electrical circuit.

2. The machine of claim 1 wherein said switch is mounted directly upon said frame.

3. The machine of claim 1 wherein said switch is mounted on a flexible cable for finger on and off operation by the fingers of the same hand that the artist uses to grip the needle bar housing during a tattooing procedure.

4. The machine of claim 3 wherein said flexible cable is stiffened just sufficiently to have a contour to which it returns after being flexed to a different contour during use in a tattooing procedure.

5. The machine of claim 1 including a radio signal receiver mounted on said frame in a relationship for effecting operation of said switch.

6. The machine of claim 5 additionally including a discretely separate foot-operated switch including a transmitter for transmitting radio signals to said radio signal receiver.

7. The machine of claim 1 wherein said electrical circuit for operating said reciprocating motion generator comprises said needle bar housing as a grounded part of said electrical circuit and wherein said switch comprises said needle bar housing and a conductive ring member for fitting on the finger of a tattoo artist's hand, said ring member being a part of said ground terminal connected to the negative terminal of said battery, whereby said electrical circuit for operating said reciprocating motion generator is closed when said ring member is put in conducive contact with said needle bar housing and is opened when said ring member is removed from electrical contact with said needle bar housing.

8. An improved method for a tattooing artist to conduct a tattooing procedure, comprising:
   (a) forming a compact battery powered tattooing machine comprising
      (i) a frame having forward and rearward locations plus a horizontal base bar and a back shelf,
      (ii) a needle bar housing removably mounted on said frame at a forward location,
      (iii) a tattoo needle assembly including, a needle bar supported by said needle bar housing in a manner for reciprocating motion of said entire tattoo needle assembly,
      (iv) a generator of reciprocating motion mounted on said frame for effecting reciprocating motion of said tattoo needle assembly, said generator including
         (a) at least one electromagnet mounted on said-base bar and
         (b) a make and break mechanism, said make and break mechanism including
            (b-1) an electrical contact member mounted in spaced relationship above said electromagnet, plus
            (b-2) a leaf spring assembly mounted at one end to said back shelf of said frame and having a free end extending between said electromagnet and said contact member, with said free end biased toward electrical contact with said contact member,
            (b-3) plus an armature bar secured to said leaf spring assembly and actuated by said electromagnet to make and break electrical contact of said leaf spring assembly with said contact member in an exceedingly rapid manner to thereby generate said reciprocating motion,
      (v) said tattoo needle assembly being connected to said armature bar for direct receipt of said reciprocating motion,
      (vi) a battery of at least 9 volts carried by said frame at a rearward location, and having a positive terminal and a negative terminal,
      (vii) an electrical circuit carried by said frame for operating said reciprocating motion generator, said electrical circuit including an energy line connected to the positive terminal of said battery and a ground terminal connected to the negative terminal of said battery,
      (viii) a rheostat interposed in said electrical circuit on said frame for adjusting the level of energy passing therethrough so as to alter the level of the action by said reciprocating motion generator in a manner dependent upon the nature of the tattoo needle assembly selected for use in the tattooing machine, and
      (ix) a switch carried by said frame and interposed in said electrical circuit to open and close said electrical circuit,
   (b) gripping the needle bar housing of said tattooing machine by the fingers of the tattoo artist's hand, and
   (c) conducting the tattooing procedure without any drag of a clip cord connected to said tattooing machine from a remote power source and thus without any drag interfering with the operator's hand movement during the tattooing procedure.

9. The method of claim 8 wherein said tattoo artist turns said switch of said tattoo machine to an on/off condition from a remote location not connected by any cord or wire to said tattooing machine.

10. The method of claim 8 including the step of adjusting the level of energy passing through said electrical circuit by adjusting a rheostat mounted on said tattooing machine itself.

11. The combination of a tattooing machine and a subassembly for electrically powering said tattooing machine,
   (a) wherein said tattooing machine is of the type having a base frame equipped with a rearwardly projecting back shelf, a needle bar housing removably mounted on said base frame at a forward location, a tattoo needle assembly including a needle bar supported by said needle bar housing for reciprocating motion of said entire tattoo needle assembly, a generator of reciprocating motion mounted on said base frame for effecting reciprocating motion of said tattoo needle assembly, said generator including at least one electromagnet in combination with a make and break mechanism having an electrical contact member mounted in spaced relationship to said electromagnet, plus a leaf spring assembly mounted at one end to said back shelf of said base frame and having a free end extending between said electromagnet and said contact member, with said free end biased toward electrical contact with said contact member, plus an armature bar secured to said leaf spring assembly and actuated by said electromagnet to make and break electrical contact of said leaf spring assembly with said contact member in an exceedingly rapid manner to thereby generate said reciprocating motion, said tattoo needle assembly being mounted on said armature bar for direct receipt of said reciprocating motion, and electrically conductive lines for operating said reciprocating motion generator, said electrically conductive lines including an energy-receiving terminal and a ground terminal, and
   (b) wherein said subassembly comprises:
      (i) a subframe having a forward shelf capable of being removably fastened to said rearwardly projecting back shelf of said tattoo machine frame in a manner such that said shelves are in overlapping relationship and in a manner such that said subframe moves with said tattooing machine frame as a structure unified to said tattooing machine frame,
      (ii) a battery of at least 9 volts carried by said subframe and having a positive terminal and a negative terminal,
      (iii) a subassembly ground terminal for conductive connection to the ground terminal of said tattooing machine, said subassembly ground terminal being connected to said negative terminal of said battery,
      (iv) an energy terminal for electrical connection to said energy-receiving terminal of said tattooing machine,
      (v) a subassembly energy line extending between said positive terminal of said battery and said energy terminal,
      (vi) a rheostat interposed in said energy line for adjusting the level of energy passing through said energy line so as to permit adjustment of the level of the energy fed to the reciprocating motion generator in a manner dependent upon the nature of the needle assembly selected for use in the tattooing machine, and (vii) a switch for interrupting or allowing the movement of electrical energy through said tattooing machine electrically conductive lines for operating said reciprocating motion generator.

12. The combination of claim 11 wherein said switch is mounted directly upon said subframe.

13. The combination of claim 11 wherein said switch is mounted on a flexible cable for finger on/off operation by fingers of the same hand of a tattoo artist that the artist uses to grip the needle bar housing during a tattooing operation.

14. The combination of claim 13 wherein said flexible cable is stiffened just sufficiently to have a contour to which it returns after being flexed to a different contour during use in a tattooing operation.

15. The combination of claim 11 including a radio signal receiver mounted on said subassembly in a relationship for effecting operation of said switch.

16. The combination of claim 15 additionally including a discretely separate foot-operated switch including a transmitter for transmitting radio signals to said radio signal receiver.

17. The combination of claim 11 wherein said electrical circuit for operating said reciprocating motion generator comprises said needle bar housing as a grounded part of said electrical circuit and wherein said switch comprises said needle bar housing and a ring member for fitting on the finger of a tattoo artist's hand, said ring member being a part of said ground terminal connected to the negative terminal of said battery, whereby said electrical circuit for operating said reciprocating motion generator is closed when said ring member is put in conducive contact with said needle bar housing and is opened when said ring member is removed from electrical contact with said needle bar housing.

18. A method of tattooing comprising
   (a) forming a tattooing machine of the type having a base frame equipped with a rearwardly projecting back shelf, a needle bar housing removably mounted on said base frame at a forward location, a tattoo needle assembly including a needle bar supported by said needle bar housing for reciprocating motion of said entire tattoo needle assembly, a generator of reciprocating motion mounted on said base frame for effecting reciprocating motion of said tattoo needle assembly, said generator including at least one electromagnet in combination with a make and break mechanism having an electrical contact member mounted in spaced relationship to said electromagnet, plus a leaf spring assembly mounted at one end to said back shelf of said base frame and having a free end extending between said electromagnet and said contact member, with said free end biased toward electrical contact with said contact member, plus an armature bar secured to said leaf spring assembly and actuated by said electromagnet to make and break electrical contact of said leaf spring assembly with said contact member in an exceedingly rapid manner to thereby generate said reciprocating motion, said tattoo needle assembly being mounted on said armature bar for direct receipt of said reciprocating motion, and electrically conductive lines for operating said reciprocating motion generator, said electrically conductive lines including an energy-receiving terminal and a ground terminal,
   (b) forming a subassembly comprising:
      (i) a subframe having a forward shelf capable of being removably fastened to said rearwardly projecting back shelf of said tattoo machine base frame in a manner such that said shelves are in overlapping relationship and in a manner such that said subframe moves with said tattooing machine base frame as a structure unified to said tattooing machine frame,
      (ii) a battery of at least 9 volts carried by said subframe and having a positive terminal and a negative terminal,
      (iii) a subassembly ground terminal for electrical connection to the ground terminal of said tattooing machine, said subassembly ground terminal being electrically connected to said negative terminal of said battery,
      (iv) an energy terminal for electrical connection to said energy-receiving terminal of said tattooing machine,
      (v) a subassembly energy line extending between said positive terminal of said battery and said energy terminal,
      (vi) a rheostat interposed in said energy line for adjusting the level of energy passing through said energy line so as to permit adjustment of the level of the energy fed to the reciprocating motion generator in a manner dependent upon the nature of the needle assembly selected for use in the tattooing machine, and
      (vii) a switch for interrupting or allowing the movement of electrical energy through said tattooing machine electrically conductive lines for operating said reciprocating motion generator,
   (c) removably fastening said forward shelf of said subframe to said rearwardly projecting back shelf of said tattoo machine base frame in a manner such that said shelves are in overlapping relationship and said subframe moves with said tattooing machine frame as a structure unified to said tattooing machine frame,
   (d) conductively connecting said subassembly ground terminal to said ground terminal of said tattooing machine,
   (e) conductively connecting said energy terminal of said subassembly to said energy-receiving terminal of said tattooing machine,
   (f) gripping the needle bar housing of said tattooing machine by the fingers of the tattoo artist's hand, and
   (g) conducting the tattooing procedure without any drag of a clip cord connected to said tattooing machine from a remote power source and-thus without any drag interfering with the operator's hand movement during the tattooing procedure.

19. A new article of manufacture entirely separate from a tattooing machine: A subassembly for removable mounting to a tattooing machine of the type having a base frame with a back shelf and an electromagnetic generator of reciprocating motion and a ground terminal and an energy-receiving terminal, said subassembly comprising : subframe with a forward shelf, a battery mounted on said subframe and having a positive and a negative terminal, a ground terminal conductively connected to said negative terminal of said battery and adapted to be electrically connected to the ground terminal on a tattooing machine, an energy line extending from said positive terminal of said battery to an energy terminal on said subframe, a rheostat interposed in said energy line for adjusting the power level of energy passing through said energy line, and a switch, said subframe of said subassembly being attachable at its forward shelf to the back shelf of said base frame in a manner such that said shelves overlap and effectively cause said subframe to move as a unit with said base frame.

* * * * *